(12) United States Patent
Sakamoto et al.

(10) Patent No.: US 12,283,048 B2
(45) Date of Patent: Apr. 22, 2025

(54) DIAGNOSIS SUPPORT DEVICE, DIAGNOSIS SUPPORT SYSTEM, AND DIAGNOSIS SUPPORT METHOD

(71) Applicants: TERUMO KABUSHIKI KAISHA, Tokyo (JP); Rokken Inc., Sakai (JP)

(72) Inventors: Yasukazu Sakamoto, Hiratsuka (JP); Itaru Okubo, Kanagawa (JP); Katsuhiko Shimizu, Fujinomiya (JP); Hiroyuki Ishihara, Tokyo (JP); Ryosuke Saga, Osaka (JP); Thomas Henn, Sakai (JP); Clément Jacquet, Sakai (JP); Nuwan Herath, Sakai (JP); Iselin Erikssen, Sakai (JP)

(73) Assignees: TERUMO KABUSHIKI KAISHA, Tokyo (JP); ROKKEN INC., Sakai (JP)

( * ) Notice: Subject to any disclaimer, the term of this patent is extended or adjusted under 35 U.S.C. 154(b) by 690 days.

(21) Appl. No.: 17/487,843

(22) Filed: Sep. 28, 2021

(65) Prior Publication Data

US 2022/0028079 A1 Jan. 27, 2022

Related U.S. Application Data

(63) Continuation of application No. PCT/JP2020/014276, filed on Mar. 27, 2020.

(30) Foreign Application Priority Data

Mar. 29, 2019 (JP) ................................ 2019-066466

(51) Int. Cl.
*G06T 7/00* (2017.01)
*A61B 8/00* (2006.01)
*A61B 8/12* (2006.01)

(52) U.S. Cl.
CPC .............. *G06T 7/0014* (2013.01); *A61B 8/12* (2013.01); *A61B 8/466* (2013.01); *A61B 8/54* (2013.01);
(Continued)

(58) Field of Classification Search
CPC ......... G06T 7/0014; A61B 8/12; A61B 8/466; A61B 8/54
See application file for complete search history.

(56) References Cited

U.S. PATENT DOCUMENTS 6,181,810 B1 1/2001 Zhang et al.
6,251,072 B1 6/2001 Ladak et al.
(Continued)

FOREIGN PATENT DOCUMENTS

CN 105120764 A 12/2015
CN 107847135 A 3/2018
(Continued)

OTHER PUBLICATIONS

International Search Report (PCT/ISA/210) with translation and Written Opinion (PCT/ISA/237) mailed on Jun. 30, 2020, by the Japan Patent Office as the International Searching Authority for International Application No. PCT/JP2020/014276.
(Continued)

*Primary Examiner* — David Bilodeau
(74) *Attorney, Agent, or Firm* — Buchanan Ingersoll & Rooney PC

(57) ABSTRACT

A diagnosis support device includes a control unit that correlates a plurality of pixels included in a two-dimensional image with two or more classes including a biological tissue class, the two-dimensional image being generated by using a signal of a reflected wave of ultrasound transmitted inside a biological tissue through which blood passes and the two-dimensional image including the biological tissue, gen-
(Continued)

erates a three-dimensional image of the biological tissue from a pixel group correlated with the biological tissue class, and performs control of displaying the generated three-dimensional image of the biological tissue.

20 Claims, 12 Drawing Sheets

(52) U.S. Cl.
CPC ............... *G06T 2207/10136* (2013.01); *G06T 2207/20081* (2013.01); *G06T 2207/20084* (2013.01); *G06T 2207/30101* (2013.01)

(56) References Cited

U.S. PATENT DOCUMENTS

| | | | |
|---|---|---|---|
| 6,385,332 | B1 | 5/2002 | Zahalka et al. |
| 10,292,676 | B2* | 5/2019 | Rajguru ................... A61B 8/12 |
| 2005/0249391 | A1 | 11/2005 | Kimmel et al. |
| 2008/0107315 | A1 | 5/2008 | Kimmel et al. |
| 2009/0259128 | A1* | 10/2009 | Stribling ................ A61B 8/445 |
| | | | 600/459 |
| 2010/0215238 | A1 | 8/2010 | Lu et al. |
| 2011/0152684 | A1 | 6/2011 | Altmann et al. |
| 2012/0078099 | A1 | 3/2012 | Suri |
| 2014/0270429 | A1 | 9/2014 | Nair et al. |
| 2016/0270766 | A1 | 9/2016 | Kobayashi |
| 2019/0307428 | A1* | 10/2019 | Silberman .............. A61B 8/467 |
| 2021/0096243 | A1* | 4/2021 | Gafner ................... G01S 15/89 |

FOREIGN PATENT DOCUMENTS

| | | |
|---|---|---|
| JP | H0984793 A | 3/1997 |
| JP | 2002521168 A | 7/2002 |
| JP | 2011131062 A | 7/2011 |
| WO | 2016/187231 A1 | 11/2016 |

OTHER PUBLICATIONS

International Preliminary Report on Patentability (Form PCT/IB/373) and the Written Opinion of the International Searching Authority (Form PCT/ISA/237) issued Sep. 28, 2021, by the International Bureau of WIPO in corresponding International Application No. PCT/JP2020/014276 and an English Translation of the Written Opinion. (13 pages).

The extended European Search Report issued May 6, 2022, by the European Patent Office in corresponding European Patent Application No. 20783173.6-1224. (7 pages).

English translation of the Office Action (First Office Action Notification) issued Mar. 4, 2023, by the State Intellectual Property Office of People's Republic of China in corresponding Chinese Patent Application No. 202080025910.9. (8 pages).

* cited by examiner

DIAGNOSIS SUPPORT DEVICE, DIAGNOSIS SUPPORT SYSTEM, AND DIAGNOSIS SUPPORT METHOD

CROSS-REFERENCES TO RELATED APPLICATIONS

This application is a continuation of International Application No. PCT/JP2020/014276 filed on Mar. 27, 2020, which claims priority to Japanese Patent Application No. 2019-066466 filed on Mar. 29, 2019, the entire content of both of which is incorporated herein by reference.

FIELD OF THE DISCLOSURE

The present disclosure generally relates to a diagnosis support device, a diagnosis support system, and a diagnosis support method.

BACKGROUND DISCUSSION

U.S. Patent Application Publication No. 2010/0215238 and U.S. Pat. Nos. 6,385,332 and 6,251,072 disclose a technique in which a contour of a cardiac cavity or a blood vessel captured in an image acquired by a medical image system such as an magnetic resonance imaging (MRI) system, an X-rays computed tomography (CT) image system, or an ultrasound (US) image system is detected, and an image region of the cardiac cavity or the blood vessel is divided from another image region.

Treatment using intravascular ultrasound (IVUS) is widely used for an intracardiac cavity, a cardiac blood vessel, and a lower extremity arterial region. The IVUS is a device or a method that provides a two-dimensional image of a plane perpendicular to a long axis of a catheter.

Currently, an operator needs to perform an operation while reconstructing a stereoscopic structure by superimposing two-dimensional images based on the IVUS in the head of the operator, which is a barrier especially for young doctors or inexperienced doctors. In order to remove such a barrier, it is taken into consideration that a three-dimensional image representing a structure of a biological tissue such as a cardiac cavity or a blood vessel is automatically generated from a two-dimensional image based on the IVUS, and the generated three-dimensional image is displayed to an operator.

Since the IVUS uses a high frequency band of about 6 MHz to 60 MHz, minute particles are captured in a two-dimensional image based on the IVUS, and blood cell noise is particularly strongly reflected. Therefore, in the method of the related art of detecting a contour of a cardiac cavity or a blood vessel captured in an image, it can be difficult to accurately differentiate an image region of a biological tissue included in a two-dimensional image based on the IVUS from other image regions such as a blood cell. Even if a three-dimensional image can be generated according to such a method, a structure of the represented biological tissue is inaccurate, which may hinder the safety of surgery.

SUMMARY

The present disclosure improves the accuracy of a three-dimensional image representing a structure of a biological tissue, generated from a two-dimensional image based on ultrasound.

According to an aspect of the present disclosure, a diagnosis support device is disclosed, which includes a control unit that correlates a plurality of pixels included in a two-dimensional image with two or more classes including a biological tissue class, the two-dimensional image being generated by using a signal of a reflected wave of ultrasound transmitted inside a biological tissue through which blood passes and the two-dimensional image including the biological tissue, generates a three-dimensional image of the biological tissue from a pixel group correlated with the biological tissue class, and performs control of displaying the generated three-dimensional image of the biological tissue.

As one embodiment of the present disclosure, the two or more classes further include a blood cell class, and the control unit excludes a pixel group correlated with the blood cell class from the plurality of pixels to generate the three-dimensional image of the biological tissue.

As one embodiment of the present disclosure, the control unit analyzes either the pixel group correlated with the biological tissue class or the generated three-dimensional image of the biological tissue to calculate a thickness of the biological tissue, and performs control of displaying the calculated thickness of the biological tissue.

As one embodiment of the present disclosure, the two or more classes further include a medical device class, and the control unit generates a three-dimensional image of the medical device from one or more pixels correlated with the medical device class, and performs control of displaying the generated three-dimensional image of the biological tissue and the three-dimensional image of the medical device in a form distinguishable from each other.

As one embodiment of the present disclosure, the control unit executes a first classification process of correlating the plurality of pixels included in the two-dimensional image with the medical device class and one or more other classes, and a second classification process of smoothing the two-dimensional image excluding one or more pixels correlated with the medical device class in the first classification process and of correlating a pixel group included in the smoothed two-dimensional image with one or more classes including the biological tissue class.

As one embodiment of the present disclosure, the control unit executes a first classification process of smoothing the two-dimensional image and of correlating the plurality of pixels included in the two-dimensional image before being smoothed with the medical device class and one or more other classes, and a second classification process of correlating, with one or more classes including the biological tissue class, a pixel group included in the smoothed two-dimensional image excluding one or more pixels correlated with the medical device class in the first classification process.

As one embodiment of the present disclosure, in a case where one or more pixels correlated with the medical device class include two or more pixels displaying different medical devices, the control unit generates the three-dimensional images of the medical devices for each medical device, and performs control of displaying the generated three-dimensional images of the medical devices in a distinguishable form for each medical device.

As one embodiment of the present disclosure, the two-dimensional image is sequentially generated while changing a transmission position of the ultrasound inside the biological tissue, and the control unit determines whether or not to correlate one or more pixels among the plurality of pixels included in the generated new two-dimensional image with the medical device class on the basis of a correlation result of the plurality of pixels included in the two-dimensional image generated before.

As one embodiment of the present disclosure, the control unit correlates the plurality of pixels included in the two-dimensional image by using a learned model.

As one embodiment of the present disclosure, the control unit processes the signal of the reflected wave to generate the two-dimensional image, and generates the three-dimensional image of the biological tissue corresponding to the generated new two-dimensional image before generating a subsequent two-dimensional image each time the new two-dimensional image is generated.

As one embodiment of the present disclosure, the control unit generates the two-dimensional image at a speed of 15 times or more and 90 times or less per second (i.e., at a speed of 15 times to 90 times per second).

According to another aspect of the present disclosure, a diagnosis support system is disclosed, which includes the diagnosis support device; and a probe that transmits the ultrasound inside the biological tissue and inputs the signal of the reflected wave to the control unit.

According to still another aspect of the present disclosure, a diagnosis support method is disclosed, which includes transmitting, by a probe, ultrasound inside a biological tissue through which blood passes; correlating, by a diagnosis support device, a plurality of pixels included in a two-dimensional image that is generated by using a signal of a reflected wave of the ultrasound and includes the biological tissue with two or more classes including a biological tissue class; generating, by the diagnosis support device, a three-dimensional image of the biological tissue from a pixel group correlated with the biological tissue class; and displaying, by a display, the three-dimensional image of the biological tissue generated by the diagnosis support device.

According to a further aspect, a non-transitory computer readable medium (CRM) storing computer program code executed by a computer processor that executes a process for diagnosis support is disclosed, the process comprising: correlating a plurality of pixels included in a two-dimensional image with two or more classes including a biological tissue class, the two-dimensional image being generated by using a signal of a reflected wave of ultrasound transmitted inside a biological tissue through which blood passes and the two-dimensional image including the biological tissue; generating a three-dimensional image of the biological tissue from a pixel group correlated with the biological tissue class; and displaying the generated three-dimensional image of the biological tissue.

According to one embodiment of the present disclosure, the accuracy of a three-dimensional image representing a structure of a biological tissue, generated from a two-dimensional image of ultrasound, can be improved.

DETAILED DESCRIPTION

Figure 1:
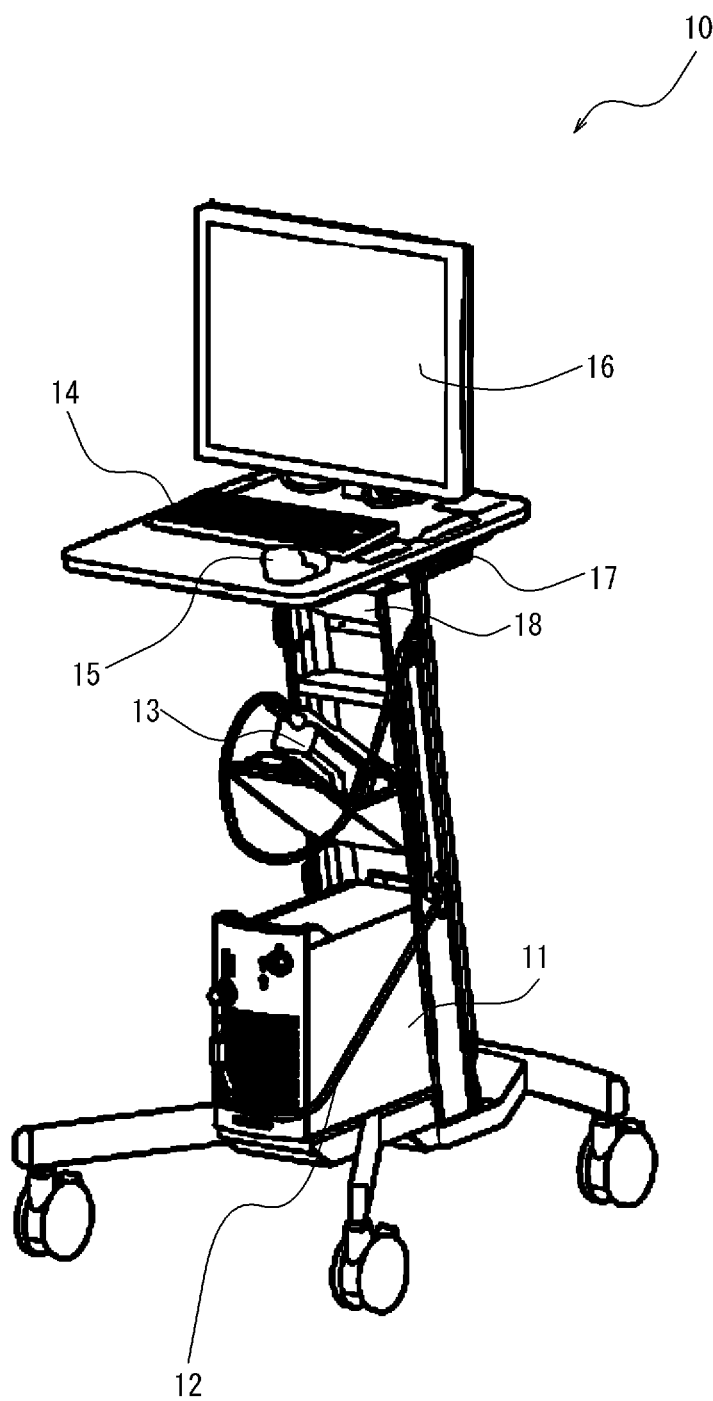
FIG. 1 is a perspective view of a diagnosis support system according to an embodiment of the present disclosure.

Set forth below with reference to the accompanying drawings is a detailed description of embodiments of a diagnosis support device, a diagnosis support system, and a diagnosis support method. Note that since embodiments described below are preferred specific examples of the present disclosure, although various technically preferable limitations are given, the scope of the present disclosure is not limited to the embodiments unless otherwise specified in the following descriptions.

In each drawing, the same or corresponding portion is given the same reference numeral. In the description of the present embodiment, the description of the same or corresponding portion will be omitted or made briefly as appropriate.

Figure 2:
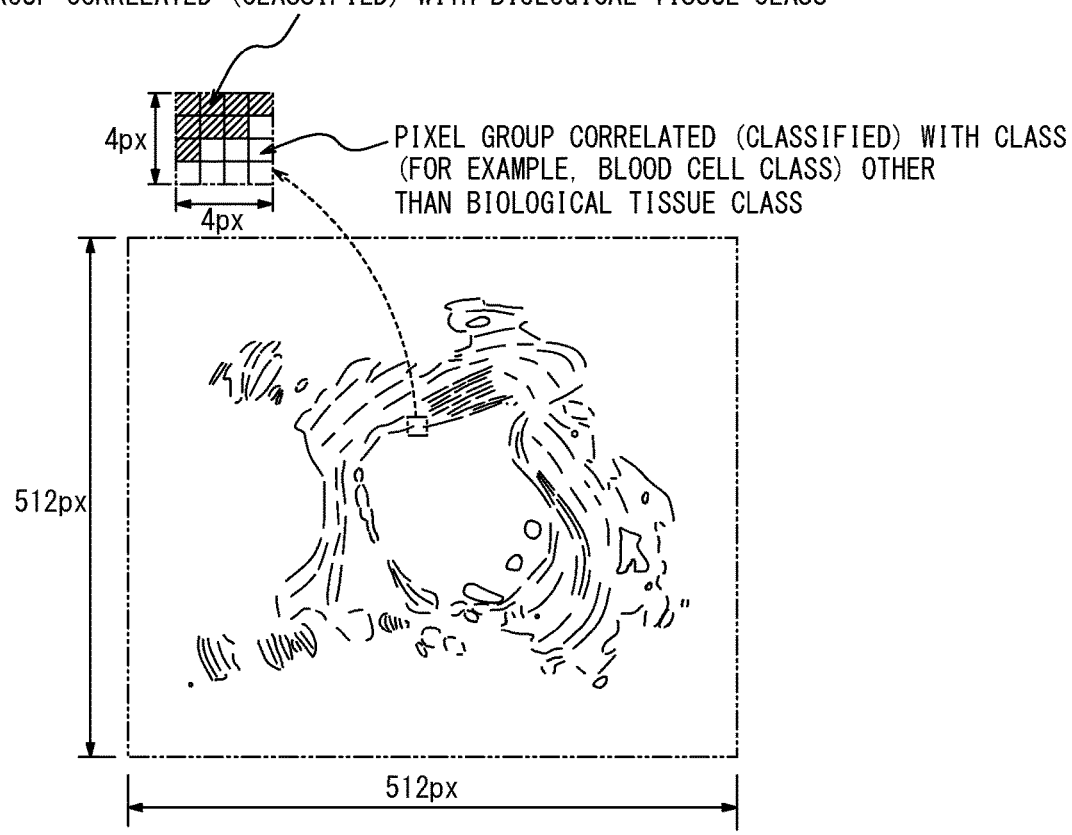
FIG. 2 is a diagram illustrating an example of classifying a plurality of pixels included in a two-dimensional image according to the embodiment of the present disclosure.

An outline of the present embodiment will be described with reference to FIGS. 1 and 2.

In the present embodiment, a diagnosis support device 11 correlates a plurality of pixels included in a two-dimensional image including a biological tissue, generated by processing a signal of a reflected wave of ultrasound transmitted inside the biological tissue through which blood passes, with two or more classes including biological tissue classes. The phrase "correlates, with classes," a plurality of pixels included in a two-dimensional image refers to assigning a label such as a biological tissue label to each pixel or classifying each pixel as a class such as a biological tissue class in order to identify the type of a target object such as a biological tissue displayed at each pixel of the two-dimensional image. In the present embodiment, the diagnosis support device 11 generates a three-dimensional image of the biological tissue from a pixel group correlated with the biological tissue class. That is, the diagnosis support device 11 generates a three-dimensional image of the biological tissue from the pixel group classified as the biological tissue class. A display 16 displays the three-dimensional image of the biological tissue generated by the diagnosis support device 11. In the example illustrated in FIG. 2, a plurality of pixels included in a two-dimensional image, for example, of 512 pixels times (x) 512 pixels, that is, 262,144 pixels are classified into two or more classes including the biological tissue class and other classes such as a blood cell class. In a region of 4 pixels times (x) 4 pixels enlarged and displayed in FIG. 2, half of 16 pixels, that is, 8 pixels are a pixel group classified as the biological tissue class, and the remaining 8 pixels are a pixel group classified as a class different from the biological tissue class. In FIG. 2, a pixel group of 4 pixels times (x) 4 pixels that is a part of a plurality of pixels included in a two-dimensional image of 512 pixels times (x) 512 pixels, is enlarged and displayed, and, for convenience of description, the pixel group classified as the biological tissue class is hatched.

According to the present embodiment, the accuracy of a three-dimensional image representing a structure of a biological tissue, which is generated from the two-dimensional image based on ultrasound, can be improved.

In the present embodiment, the diagnosis support device 11 uses a two-dimensional image based on IVUS as the two-dimensional image based on ultrasound.

The IVUS is used, for example, during an intervention. The reasons for this include, for example, the following reasons: to determine the property of biological tissue such as an intracardiac cavity; to check a position where an implanted object such as a stent is to be disposed or a position where the implanted object is disposed; and to check positions of a catheter other than an IVUS catheter and a guidewire or the like while using a two-dimensional image in real time In accordance with an exemplary embodiment, the "catheter other than an IVUS catheter" described above is, for example, a stent indwelling catheter or an ablation catheter.

According to the present embodiment, an operator does not need to perform an operation while reconstructing a stereoscopic structure by superimposing two-dimensional images based on the IVUS in the head of the operator, which makes the operation easier, especially for younger or inexperienced doctors. There are no barriers, especially for younger or inexperienced doctors.

In the present embodiment, the diagnosis support device 11 is configured to be able to determine a positional relationship between catheters other than an IVUS catheter or implanted objects, or biological tissue property with a three-dimensional image during the operation.

In the present embodiment, the diagnosis support device 11 can be configured to be able to update the three-dimensional image in real time to guide, for example, an IVUS catheter.

In procedures such as ablation, there is a demand to determine the energy for ablation by taking into consideration a thickness of a blood vessel or a cardiac muscle region. When an atherectomy device that scrapes calcified lesions or plaque is used, there is also a demand to perform procedures by taking into consideration a thickness of biological tissue. In the present embodiment, the diagnosis support device 11 is configured to be able to display a thickness of biological tissue, for example a blood vessel or a cardiac muscle region.

In the present embodiment, the diagnosis support device 11 is configured to be able to continuously provide a three-dimensional structure of a site that is observable with a radial blood vessel by continuously updating a three-dimensional image by using IVUS continuous images that are constantly updated.

In order to represent a cardiac cavity structure from a two-dimensional image based on IVUS, catheters other than an IVUS catheter in a blood cell region, a cardiac muscle region, and an intracardiac cavity are required to be differentiated. In the present embodiment, the differentiation is possible and only the cardiac muscle region can be displayed.

Since the IVUS uses a high frequency band, for example, of about 6 MHz to 60 MHz, blood cell noise can be strongly reflected, but, in the present embodiment, it is possible to make a difference between the biological tissue region and the blood cell region.

In order to execute a process of representing the cardiac cavity structure from the two-dimensional image based on the IVUS updated at a speed of 15 frames per second (FPS) or more and 90 FPS or less in real time (i.e., 15 FPS to 90 FPS), the time for processing one image is restricted to 11 msec or more and 66 msec or less (i.e., 11 msec to 66 msec). In the present embodiment, the diagnosis support device 11 is configured to be able to cope with such a restriction.

In the present embodiment, the diagnosis support device 11 is configured to be able to darken an image on which biological tissue property is specified, a blood cell region is removed, or a position of a catheter other than an IVUS catheter is specified in a three-dimensional space, and compute a process before a three-dimensional image is drawn for a time until the subsequent frame image arrives, that is, within the time when the real-time property is established.

In the present embodiment, the diagnosis support device 11 is configured to be able to provide not only a structure but also additional information that meets a doctor's request, such as information regarding lime or plaque.

A configuration of a diagnosis support system 10 according to the present embodiment will be described with reference to FIG. 1.

The diagnosis support system 10 includes the diagnosis support device 11, a cable 12, a drive unit 13, a keyboard 14, a mouse 15, and the display 16.

In accordance with an exemplary embodiment, the diagnosis support device 11 can be a dedicated computer specialized for image diagnosis in the present embodiment, but may be a general-purpose computer such as a personal computer (PC).

The cable 12 is used to connect the diagnosis support device 11 to the drive unit 13.

Figure 3:
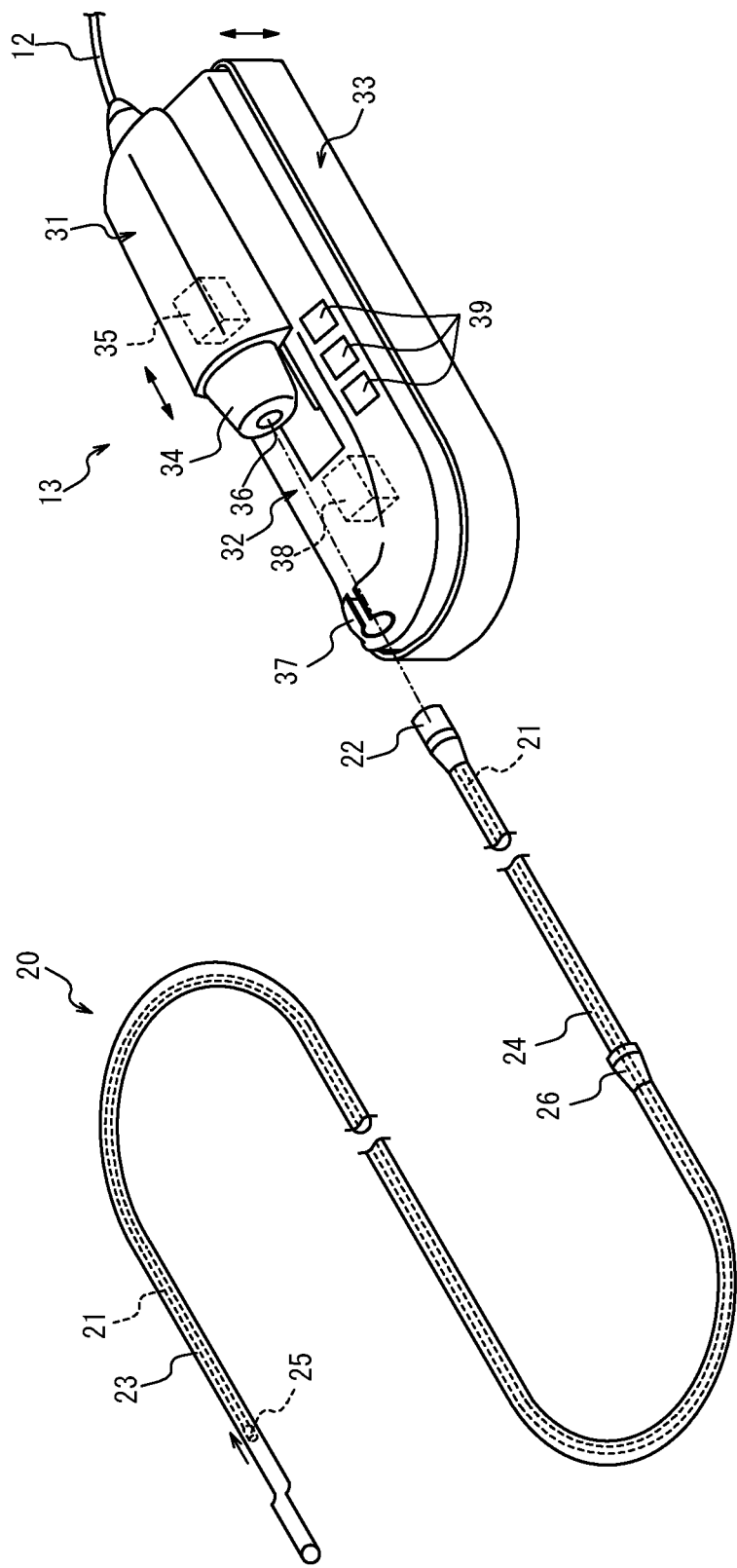
FIG. 3 is a perspective view of a probe and a drive unit according to the embodiment of the present disclosure.

The drive unit 13 is a device used by being connected to a probe 20 illustrated in FIG. 3 to drive the probe 20. The drive unit 13 is also called a motor drive unit (MDU). The probe 20 is applied to IVUS. The probe 20 is also called an IVUS catheter or an image diagnosis catheter.

The keyboard 14, the mouse 15, and the display 16 are connected to the diagnosis support device 11 via a cable or wirelessly. The display 16 can be, for example, a liquid crystal display (LCD), an organic electro luminescence (EL) display, or a head-mounted display (HMD).

In accordance with an exemplary embodiment, the diagnosis support system 10 can further include a connection terminal 17 and a cart unit 18.

The connection terminal 17 is used to connect the diagnosis support device 11 to an external device. The connection terminal 17 is, for example, a Universal Serial Bus (USB) terminal. As the external device, for example, a recording medium such as a magnetic disk drive, a magneto-optical disk drive, or an optical disc drive may be used.

In accordance with an exemplary embodiment, the cart unit 18 can be a cart with casters for movement. The diagnosis support device 11, the cable 12, and the drive unit 13 are installed on a cart body of the cart unit 18. The keyboard 14, the mouse 15, and the display 16 are installed on a table at the top of the cart unit 18.

Configurations of the probe 20 and the drive unit 13 according to the present embodiment will be described with reference to FIG. 3.

The probe 20 can include a drive shaft 21, a hub 22, a sheath 23, an outer tube 24, an ultrasound transducer 25, and a relay connector 26.

The drive shaft 21 passes through the sheath 23 inserted into a body cavity of a living body and the outer tube 24 connected to the proximal end of the sheath 23, and extends to the inside of the hub 22 provided at the proximal end of the probe 20. The drive shaft 21 has the ultrasound transducer 25 that transmits and receives signals at its distal end, and is rotatably provided in the sheath 23 and the outer tube 24. The relay connector 26 connects the sheath 23 to the outer tube 24.

The hub 22, the drive shaft 21, and the ultrasound transducer 25 are connected to each other to be moved forward and backward in the axial direction integrally (i.e., relating to, or belonging as a part of a whole). Therefore, for example, when the hub 22 is operated to be pushed toward the distal side, the drive shaft 21 and the ultrasound transducer 25 are moved toward the distal side inside the sheath 23. For example, when the hub 22 is operated to be pulled to the proximal side, the drive shaft 21 and the ultrasound transducer 25 are moved toward the proximal side inside the sheath 23 as indicated by an arrow.

In accordance with an exemplary embodiment, the drive unit 13 can include a scanner unit 31, a slide unit 32, and a bottom cover 33.

The scanner unit 31 is connected to the diagnosis support device 11 via the cable 12. The scanner unit 31 includes a probe connection section 34 connected to the probe 20 and a scanner motor 35 that is a drive source rotating the drive shaft 21.

The probe connection section 34 is freely detachably connected to the probe 20 via an outlet 36 into which the hub 22 provided at the proximal end of the probe 20 is inserted. The proximal end of the drive shaft 21 is rotatably supported inside the hub 22, and thus the rotational force of the scanner motor 35 is transmitted to the drive shaft 21. Signals are transmitted and received between the drive shaft 21 and the diagnosis support device 11 via the cable 12. The diagnosis support device 11 generates a tomographic image of a biological lumen and performs image processing on the basis of a signal transmitted from the drive shaft 21.

The slide unit 32 mounts the scanner unit 31 to be movable forward and backward, and is mechanically and electrically connected to the scanner unit 31. The slide unit 32 includes a probe clamp section 37, a slide motor 38, and a switch group 39.

The probe clamp section 37 is provided to be disposed coaxially with the probe connection section 34 on the distal side of the probe connection section 34, and supports the probe 20 connected to the probe connection section 34.

The slide motor 38 is a drive source that generates a driving force in the axial direction. The scanner unit 31 is moved forward and backward by driving the slide motor 38, and thus the drive shaft 21 is moved forward and backward in the axial direction. The slide motor 38 can be, for example, a servo motor.

The switch group 39 can include, for example, a forward switch and a pullback switch that are pressed when the scanner unit 31 is operated to be moved forward and backward, and a scan switch that is pressed when image drawing starts and ends. The present disclosure is not limited to the example here, and various switches are included in the switch group 39 as needed.

When the forward switch is pressed, the slide motor 38 rotates in the forward direction and thus the scanner unit 31 is moved forward. On the other hand, when the pullback switch is pressed, the slide motor 38 rotates in the reverse direction, and thus the scanner unit 31 is moved backward.

When the scan switch is pressed, image drawing (i.e., image generation) is started, the scanner motor 35 is driven, and the slide motor 38 is driven to move the scanner unit 31 backward. An operator connects the probe 20 to the scanner unit 31 in advance such that the drive shaft 21 is moved toward the proximal side in the axial direction while rotating at the start of image drawing. The scanner motor 35 and the slide motor 38 are stopped when the scan switch is pressed again, and the image drawing ends.

The bottom cover 33 covers the bottom of the slide unit 32 and the entire circumference of the side surface on the bottom side, and freely comes close to and separates from the bottom of the slide unit 32.

Figure 4:
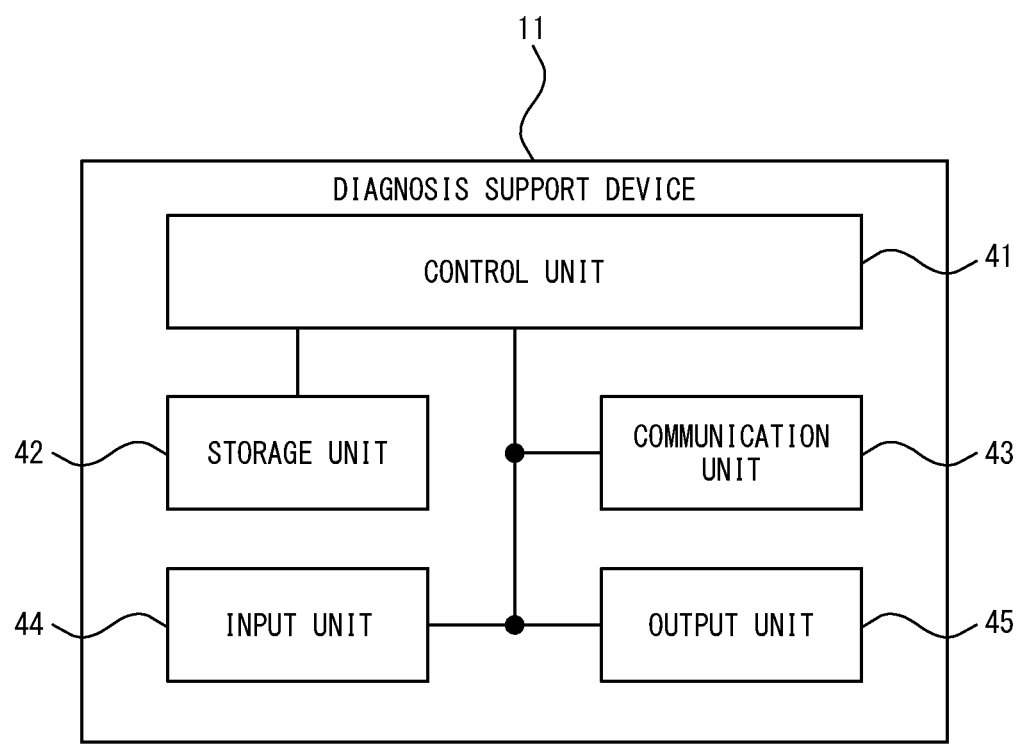
FIG. 4 is a block diagram illustrating a configuration of a diagnosis support device according to the embodiment of the present disclosure.

A configuration of the diagnosis support device 11 according to the present embodiment will be described with reference to FIG. 4.

The diagnosis support device 11 includes constituents such as a control unit 41, a storage unit 42, a communication unit 43, an input unit 44, and an output unit 45.

The control unit 41 can include one or more processors. As the processor, a general-purpose processor such as a central processing unit (CPU) or a graphic processing unit (GPU), or a dedicated processor specialized for a specific process may be used. The control unit 41 may include one or more dedicated circuits, or one or more processors may be replaced with one or more dedicated circuits in the control unit 41. As the dedicated circuit, for example, a field-programmable gate array (FPGA) or an application specific integrated circuit (ASIC) may be used. The control unit 41 controls the respective units of the diagnosis support system 10 including the diagnosis support device 11 and also executes information processing related to an operation of the diagnosis support device 11.

The storage unit 42 can include one or more memories. As the memory, for example, a semiconductor memory, a magnetic memory, or an optical memory may be used. As the semiconductor memory, for example, a random access memory (RAM) or a read only memory (ROM) may be used. As the RAM, for example, a static random access memory (SRAM) or a dynamic random access memory (DRAM) may be used. As the ROM, for example, an electrically erasable programmable read only memory (EEPROM) may be used. The memory functions as, for example, a main storage device, an auxiliary storage device, or a cache memory. The storage unit 42 stores information used for the operation of the diagnosis support device 11 and information obtained through the operation of the diagnosis support device 11.

The communication unit 43 includes one or more communication interfaces. As the communication interface, a wired local area network (LAN) interface, a wireless LAN interface, or an image diagnosis interface that receives and analog to digital converts (ND) IVUS signals may be used. The communication unit 43 receives information used for the operation of the diagnosis support device 11, and transmits information obtained through the operation of the diagnosis support device 11. In the present embodiment, the drive unit 13 is connected to the image diagnosis interface included in the communication unit 43.

The input unit 44 includes one or more input interfaces. As the input interface, for example, a USB interface or a High-Definition Multimedia Interface HDMI® interface may be used. The input unit 44 receives an operation for inputting information used for the operation of the diagnosis support device 11. In the present embodiment, the keyboard 14 and the mouse 15 are connected to the USB interface included in the input unit 44, but the keyboard 14 and the mouse 15 may be connected to the wireless LAN interface included in the communication unit 43.

The output unit 45 includes one or more output interfaces. As the output interface, for example, a USB interface or an HDMI interface may be used. The output unit 45 outputs information obtained through the operation of the diagnosis support device 11. In the present embodiment, the display 16 is connected to the HDMI interface included in the output unit 45.

The function of the diagnosis support device 11 is realized by the processor included in the control unit 41 executing a diagnosis support program according to the present embodiment. That is, the function of the diagnosis support device 11 can be realized by software. The diagnosis support program is a program causing a computer to execute a process in a step included in the operation of the diagnosis support device 11 such that the computer can realize a function corresponding to the process in the step. That is, the diagnosis support program is a program causing the computer to function as the diagnosis support device 11.

The program can be recorded on a computer readable recording medium. As the computer readable recording medium, for example, a magnetic recording device, an optical disc, a magneto-optical recording medium, or a semiconductor memory may be used. A distribution of the program is performed, for example, by selling, transferring, or renting a portable recording medium such as a digital versatile disc (DVD) or a compact disc read only memory (CD-ROM) on which the program is recorded. The program may be distributed by storing the program in a storage of a server and transferring the program from the server to another computer via a network. The program may be provided as a program product.

The computer temporarily stores, for example, a program recorded on a portable recording medium or a program transferred from a server in a memory. The computer reads the program stored in the memory with the processor, and execute a process according to the read program with the processor. The computer may read the program directly from a portable recording medium and execute a process according to the program. The computer may sequentially execute a process according to the received program each time the program is transferred from the server to the computer. The process may be executed according to a so-called application service provider (ASP) type service for realizing the function in accordance with only an execution instruction and result acquisition without transferring the program from the server to the computer. The program includes information used for processes executed by a computer and equivalent to the program. For example, data that is not a direct command for a computer but has the property of defining a process in the computer corresponds to "data equivalent to the program".

Some or all of the functions of the diagnosis support device 11 may be realized by a dedicated circuit included in the control unit 41. That is, some or all of the functions of the diagnosis support device 11 may be realized by hardware.

The operation of the diagnosis support system 10 according to the present embodiment will be described with reference to FIG. 5. The operation of the diagnosis support system 10 corresponds to the diagnosis support method according to the present embodiment.

Figure 5:
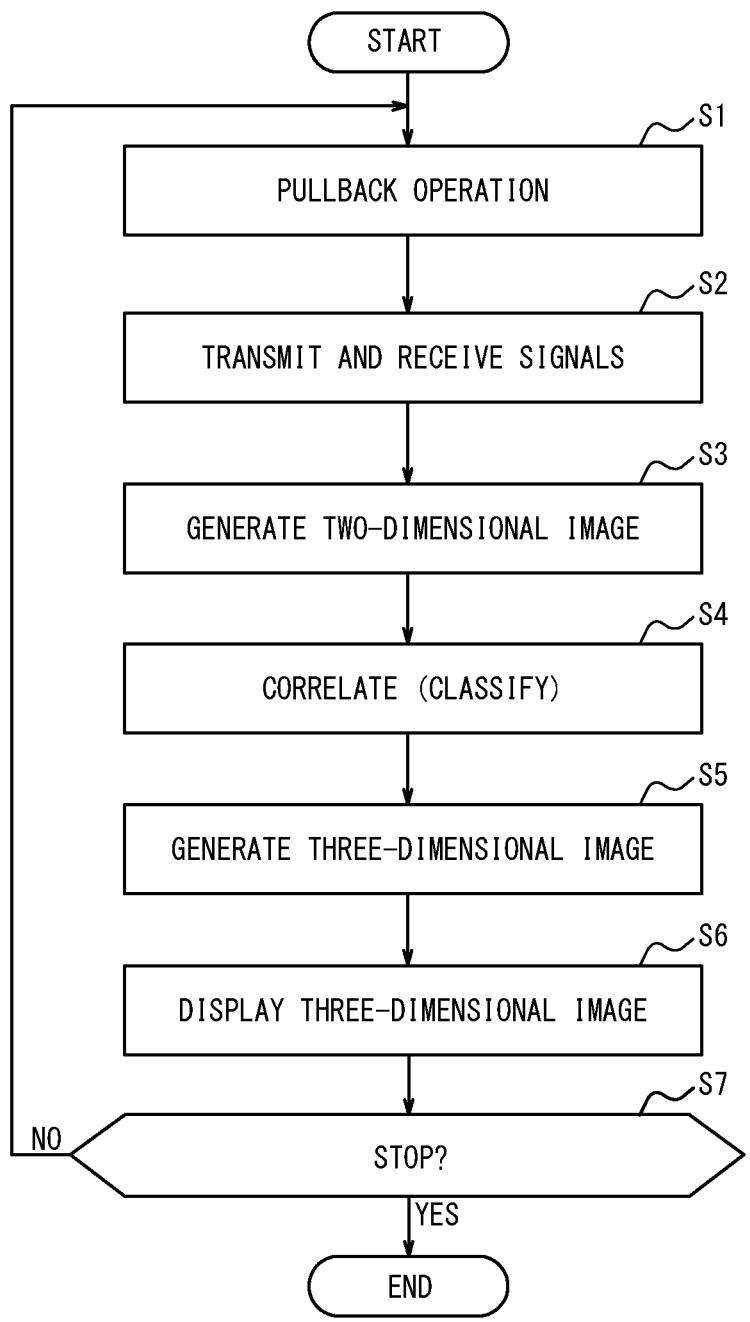
FIG. 5 is a flowchart illustrating an operation of the diagnosis support system according to the embodiment of the present disclosure.

Prior to the start of the flow in FIG. 5, the probe 20 is primed by the operator. Thereafter, the probe 20 is fitted into the probe connection section 34 and the probe clamp section 37 of the drive unit 13, and is thus connected and fixed to the drive unit 13. The probe 20 is inserted into a target site in a biological tissue through which blood passes, such as a cardiac cavity or a blood vessel.

In step S1, when the scan switch included in the switch group 39 is pressed and the pullback switch included in the switch group 39 is further pressed, a so-called pullback operation is performed. The probe 20 transmits ultrasound inside the biological tissue with the ultrasound transducer 25 that is moved backward in the axial direction due to the pullback operation.

In step S2, the probe 20 inputs a signal of a reflected wave of the ultrasound transmitted in step S1 to the control unit 41 of the diagnosis support device 11.

Specifically, the probe 20 transmits a signal of the ultrasound reflected inside the biological tissue to the diagnosis support device 11 via the drive unit 13 and the cable 12. The communication unit 43 of the diagnosis support device 11 receives the signal transmitted from the probe 20. The communication unit 43 performs A/D conversion on the received signal. The communication unit 43 inputs the signal subjected to the A/D conversion to the control unit 41.

In step S3, the control unit 41 of the diagnosis support device 11 processes the signal input in step S2 to generate a two-dimensional image based on ultrasound.

Figure 6:
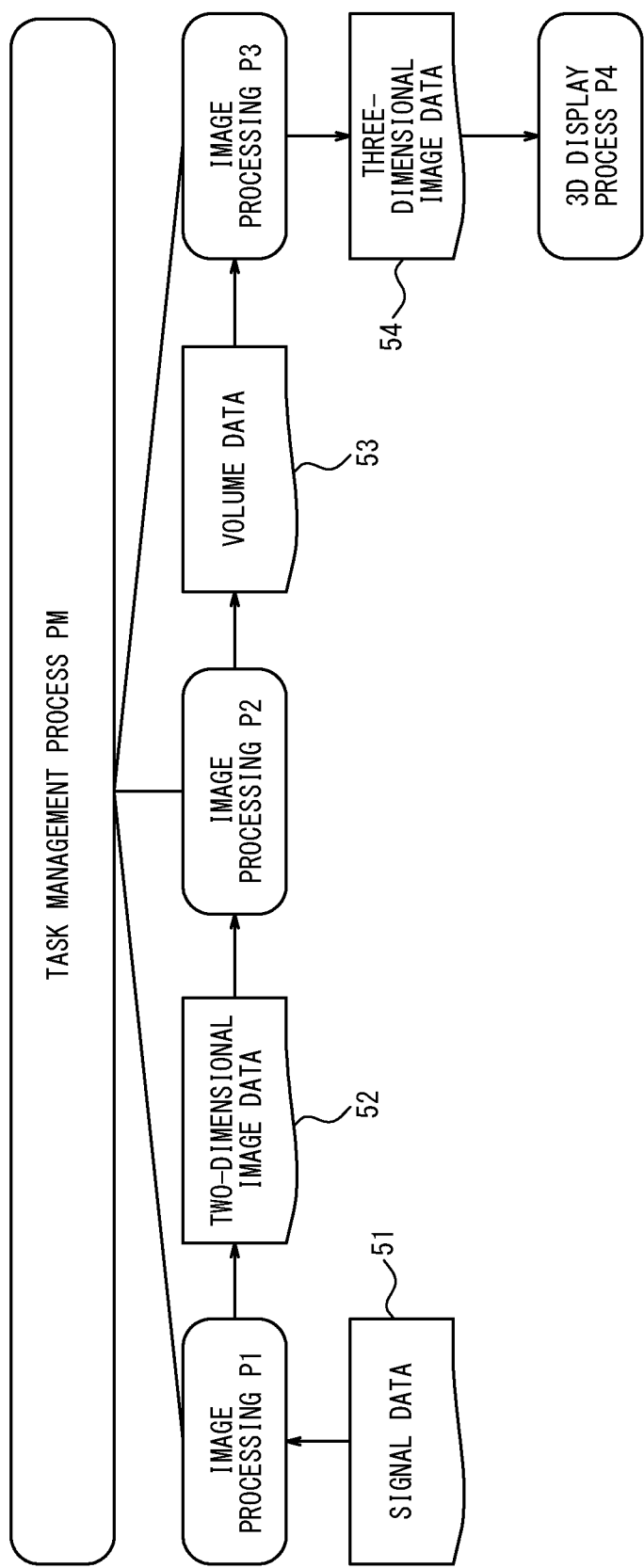
FIG. 6 is a diagram illustrating a data flow in the diagnosis support device according to the embodiment of the present disclosure.

Specifically, as illustrated in FIG. 6, the control unit 41 executes a task management process PM for managing at least image processing P1, image processing P2, and image processing P3. A function of the task management process PM is installed as one function of an operating system (OS), for example. The control unit 41 acquires the signal subjected to A/D conversion by the communication unit 43 in step S2 as signal data 51. The control unit 41 activates the image processing P1 by using the task management process PM, processes the signal data 51, and generates a two-dimensional image based on IVUS. The control unit 41 acquires, as two-dimensional image data 52, the two-dimensional image based on IVUS that is a result of the image processing P1.

In step S4, the control unit 41 of the diagnosis support device 11 classifies a plurality of pixels included in the two-dimensional image generated in step S3 into two or more classes including a biological tissue class corresponding to a pixel which displays the biological tissue. In the present embodiment, these two or more classes further include a blood cell class corresponding to a pixel displaying a blood cell contained in blood. The two or more classes further include a medical device class corresponding to a pixel displaying a medical device such as a catheter other than an IVUS catheter or a guidewire. The two or more classes may further include an implanted object class corresponding to a pixel displaying an implanted object, for example, such as a stent. The two or more classes may further include a lesion class corresponding to a pixel displaying a lesion such as lime or plaque. Each class may be subdivided. For example, the medical device class may be divided into a catheter class, a guidewire class, and other medical device classes.

Figure 7:
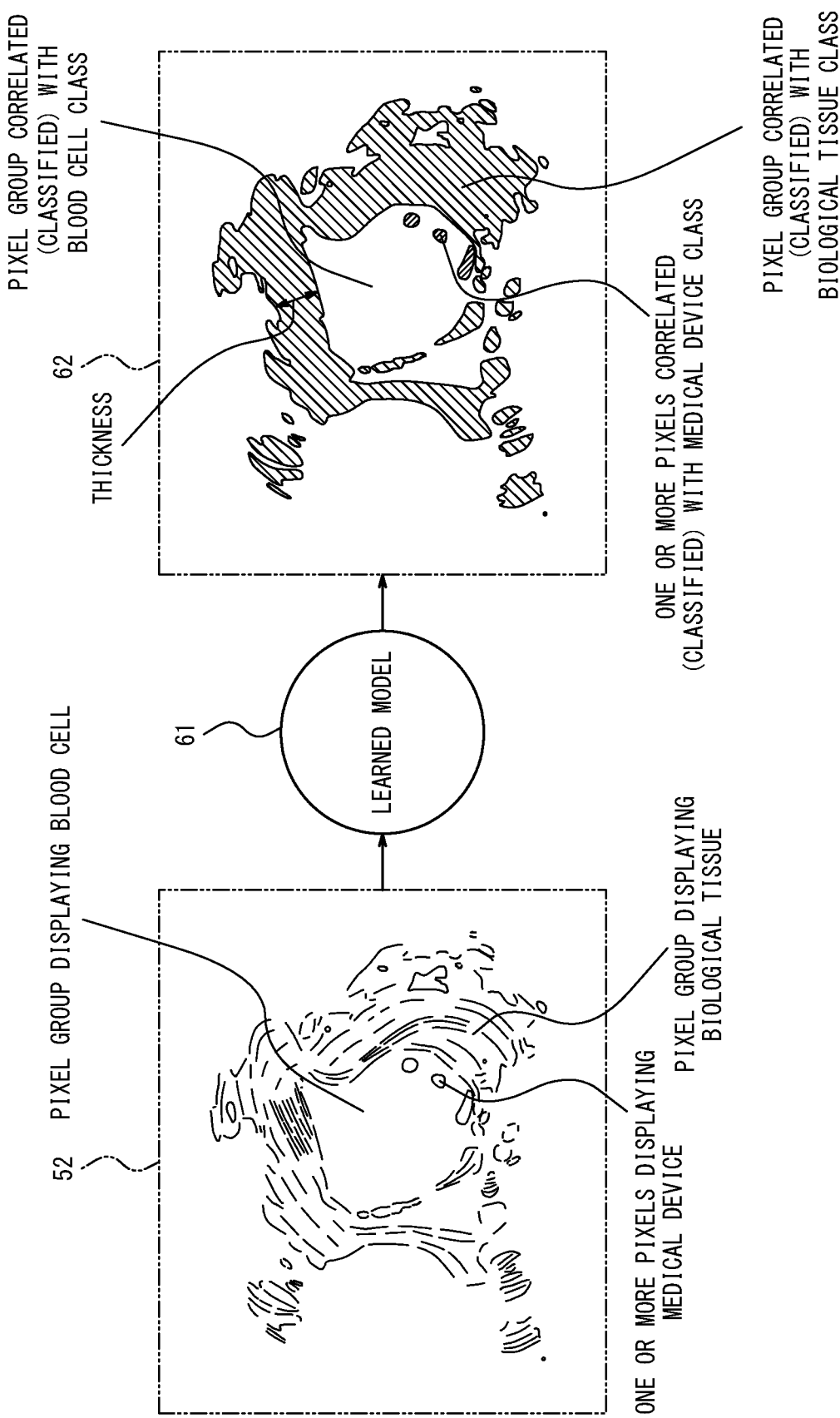
FIG. 7 is a diagram illustrating an example of input/output in a learned model according to the embodiment of the present disclosure.

Specifically, as illustrated in FIGS. 6 and 7, the control unit 41 activates the image processing P2 by using the task management process PM, and uses a learned model 61 to classify the plurality of pixels included in the two-dimensional image data 52 acquired in step S3. The control unit 41 acquires, as a classification result 62, a two-dimensional image obtained by assigning any of the biological tissue class, the blood cell class, and the medical device class to each pixel of the two-dimensional image data 52 that is a result of the image processing P2.

In step S5, the control unit 41 of the diagnosis support device 11 generates a three-dimensional image of the biological tissue from a pixel group classified as the biological tissue class in step S4. In the present embodiment, the control unit 41 generates a three-dimensional image of the biological tissue by excluding the pixel group classified as the blood cell class in step S4 from the plurality of pixels included in the two-dimensional image generated in step S3. The control unit 41 generates a three-dimensional image of the medical device from one or more pixels classified into the medical device class in step S4. In a case where one or more pixels classified as the medical device class in step S4 include two or more pixels displaying different medical devices, the control unit 41 generates three-dimensional images of the medical devices for each medical device.

Specifically, as illustrated in FIG. 6, the control unit 41 executes the image processing P2 by using the task management process PM, and generates a three-dimensional image by superimposing two-dimensional images in which a classification is assigned to each pixel of the two-dimensional image data 52 acquired in step S4. The control unit 41 acquires volume data 53 representing a stereoscopic structure for each classification, which is a result of the image processing P2. The control unit 41 activates the image processing P3 by using the task management process PM and visualizes the acquired volume data 53. The control unit 41 acquires, as three-dimensional image data 54, a three-dimensional image representing the stereoscopic structure for each classification, which is a result of the image processing P3.

As a modification example of the present embodiment, the control unit 41 may generate a three-dimensional image of the medical device on the basis of coordinates of one or more pixels classified as the medical device class in step S4. Specifically, the control unit 41 may store data indicating coordinates of the one or more pixels classified as the medical device class in step S4 as coordinates of a plurality of points present along the movement direction of the scanner unit 31 of the drive unit 13, and generate a linear three-dimensional model connecting the plurality of points along the movement direction of the scanner unit 31 as a three-dimensional image of the medical device. For example, for a medical device having a relatively small cross-section such as a catheter, the control unit 41 may dispose, as the three-dimensional image of the medical device, a three-dimensional model having a circular cross-section at a coordinate of the center of one pixel classified as the medical device class or the center of a pixel group classified as the medical device class. That is, in a case of a small object such as a catheter, a coordinate may be returned as the classification result 62 instead of a pixel or a region as a set of pixels.

In step S6, the control unit 41 of the diagnosis support device 11 controls to display the three-dimensional image of the biological tissue generated in step S5. In the present embodiment, the control unit 41 performs control of displaying the three-dimensional image of the biological tissue and the three-dimensional image of the medical device generated in step S5 in a format in which the images can be differentiated from each other. If the three-dimensional image of the medical device is generated for each medical device in step S5, the control unit 41 performs control of displaying the generated three-dimensional image of the medical device in a format in which the image can be differentiated for each medical device. The display 16 is controlled by the control unit 41 to display the three-dimensional image of the biological tissue and the three-dimensional image of the medical device.

Specifically, as illustrated in FIG. 6, the control unit 41 executes a 3D display process P4 and displays the three-dimensional image data 54 acquired in step S6 on the display 16 via the output unit 45. The three-dimensional image of the biological tissue such as a cardiac cavity or a blood vessel and the three-dimensional image of the medical device such as a catheter are displayed in a differentiated manner by coloring the images differently. Of the three-dimensional image of the biological tissue and the three-dimensional image of the medical device, an arbitrary image may be selected by using the keyboard 14 or the mouse 15. In this case, the control unit 41 receives an operation of selecting an image via the input unit 44. The control unit 41 displays the selected image on the display 16 via the output unit 45, and hides the unselected image. Any cut surface may be set by using the keyboard 14 or the mouse 15. In this case, the control unit 41 receives an operation of selecting the cut surface via the input unit 44. The control unit 41 displays a three-dimensional image cut on the selected cut surface on the display 16 via the output unit 45.

In step S7, if the scan switch included in the switch group 39 is not pressed again, the process returns to step S1 and the pullback operation is continued. As a result, two-dimensional images based on IVUS are sequentially generated while changing a transmission position of ultrasound inside the biological tissue. On the other hand, if the scan switch is pressed again, the pullback operation is stopped and the flow in FIG. 5 ends.

In the present embodiment, the image processing P1 and the 3D display process P4 are executed on the CPU, and the image processing P2 and the image processing P3 are executed on the GPU. The volume data 53 may be stored in a storage area in the CPU, but is stored in a storage area in the GPU in order to omit data transfer between the CPU and the GPU.

In particular, the respective processes such as classification, catheter detection, image interpolation, and three-dimensional processing included in the image processing P2 are executed in a general purpose graphics processing unit (GP-GPU) in the present embodiment, but may be executed in an integrated circuit such as an FPGA or an ASIC. The respective processes may be executed in series or in parallel. The respective processes may be executed via the network.

In step S4, the control unit 41 of the diagnosis support device 11 extracts the biological tissue region through region recognition instead of edge extraction as in the related art. The reason will be described.

In an IVUS image, it is conceivable to extract an edge indicating a boundary between the blood cell region and the biological tissue region for the purpose of removing the blood cell region, and reflect the edge in a three-dimensional space to create a three-dimensional image. However, edge extraction can be extremely difficult for the following reasons.

A luminance gradient at the boundary between the blood cell region and the biological tissue region is not constant, and it can be difficult to extract the edge in all IVUS images with a uniform algorithm.

In a case where a three-dimensional image is created with edges, it is not possible to represent a complicated structure, such as in a case of targeting not only a blood vessel wall but also the entire cardiac cavity.

The edge extraction is not sufficient in an image in which a blood cell region is included not only inside a biological tissue but also outside the biological tissue such as a portion where both the left and right atria are seen.

A catheter cannot be specified only by extracting an edge. In particular, in a case where a wall of the biological tissue and the catheter are in contact with each other, it is not possible to establish a boundary with the biological tissue.

When a thin wall is sandwiched with two blood cell regions in an IVUS image, it is difficult to tell which side is really a biological tissue from the edge alone.

It is also difficult to calculate a thickness of the wall of the biological tissue.

In steps S2 to S6, the control unit 41 of the diagnosis support device 11 is required to remove a blood cell component, extract an organ part, reflect information on the organ part in a three-dimensional space, and draw a three-dimensional image when three-dimensional processing is performed, but, since three-dimensional images are continuously updated in real time, these processes can be completed within a time Tx for which the images are sent. The time Tx is 1/FPS. Real-time processing cannot be realized in the related art of providing a three-dimensional image. In the method of the related art, processing is performed frame by frame, and a three-dimensional image cannot be continuously updated until the subsequent frame arrives.

As described above, in the present embodiment, each time a new two-dimensional image is generated, the control unit 41 generates a three-dimensional image of the biological tissue corresponding to the generated new two-dimensional image before the subsequent two-dimensional image is generated.

Specifically, the control unit 41 generates a two-dimensional image based on IVUS at a speed, for example, of 15 times or more per second and 90 times or less per second (i.e., 15 times per second to 90 times per second), and updates a three-dimensional image at a speed of 15 times or more and 90 times or less per second (i.e., 15 times per second to 90 times per second).

In step S4, the control unit 41 of the diagnosis support device 11 can specify a particularly small object such as a catheter by extracting a region of an object other than the biological tissue through region recognition instead of the edge extraction of the related art, and can thus deal with the following issues.

In a case where a catheter is in contact with the wall, even a human can determine that the catheter is a biological tissue from only one image.

However, a catheter can be mistaken for a thrombus or a bubble, and thus it can be difficult to determine the catheter from only one image.

Just as a human estimates a catheter position by using the past continuous images as reference information, the control unit 41 may use the past information to specify the catheter position.

In step S4, even in a case where the main body of the probe 20 is in contact with the wall surface at the center of the two-dimensional image, the control unit 41 of the diagnosis support device 11 can differentiate the probe and the wall surface by extracting a region of an object other than the biological tissue through region recognition instead of the edge extraction of the related art. That is, the control unit 41 can differentiate an IVUS catheter from a biological tissue region.

In step S4, the control unit 41 of the diagnosis support device 11 extracts the biological tissue region and the catheter region instead of edge extraction in order to represent a complicated structure, determine the biological tissue property, and search for a small object such as a catheter. Therefore, in the present embodiment, a machine learning approach can be employed. In accordance with an exemplary embodiment, the control unit 41 can directly evaluate what kind of property a portion of each pixel of an image has by using the learned model 61, and can reflect the image in which a classification is assigned in a three-dimensional space set under defined conditions. The control unit 41 superimposes the information in the three-dimensional space, performs three-dimensional processing on the basis of information stored in a three-dimensionally disposed memory space, and displays a three-dimensional image. In accordance with an exemplary embodiment, the above-mentioned processes can be updated in real time, and three-dimensional information at a position corresponding to a two-dimensional image can be updated. Computations are performed sequentially or in parallel. In particular, the processes can be performed in parallel to improve time efficiency.

In accordance with an exemplary embodiment, the machine learning refers to analyzing input data by using an algorithm, extracting useful rules or determination criteria from an analysis result, and developing the algorithm. Machine learning algorithms can be generally classified into supervised learning, unsupervised learning, reinforcement learning, and the like. In the supervised learning algorithm, a dataset of input of audio data on living body sound serving as a sample and an ultrasound image and a result of corresponding disease data is given, and machine learning is performed on the basis of the dataset. In the unsupervised learning algorithm, machine learning is performed by giving a large amount of input data. The reinforcement learning algorithm changes an environment on the basis of a solution output by the algorithm, and is modified on the basis of the reward for how correct the output solution is. A model subjected to machine learning, obtained in the above-described way, is used as the learned model 61.

In accordance with an exemplary embodiment, the learned model 61 can be trained such that a class can be specified from a sample two-dimensional image by performing machine learning in advance. A sample ultrasound image and an image in which a classification pre-labeled by a person is performed on the ultrasound image are collected at a medical institution such as a university hospital where many patients gather.

An IVUS image has high noise such as a blood cell region, and also has system noise. Thus, in step S4, the control unit 41 of the diagnosis support device 11 performs a preprocess on the image before inserting the image into the learned model 61. The preprocess can include, for example, smoothing using various filters such as simple blur, median blur, Gaussian blur, a bilateral filter, a median filter, or block averaging, image morphology such as dilation and erosion, opening and closing, morphological gradient, or top hat and black hat, or flood fill, resize, image pyramids, threshold, low path filter, high path filter, or discrete wavelet transform. However, in a case where such a process is performed on a normal CPU, there is a probability that the process alone may not be completed, for example, within 66 msec. Therefore, this process is performed on a GPU. In particular, in a machine learning approach that is constructed with multiple layers called deep learning, it has been verified that it is possible to perform a preprocess with real-time property by constructing an algorithm as the layers. In this verification, a classification accuracy, for example, of 97% or more and 42 frames per second (FPS) are achieved by using an image of 512 pixels times (x) 512 pixels or more.

Figure 14:
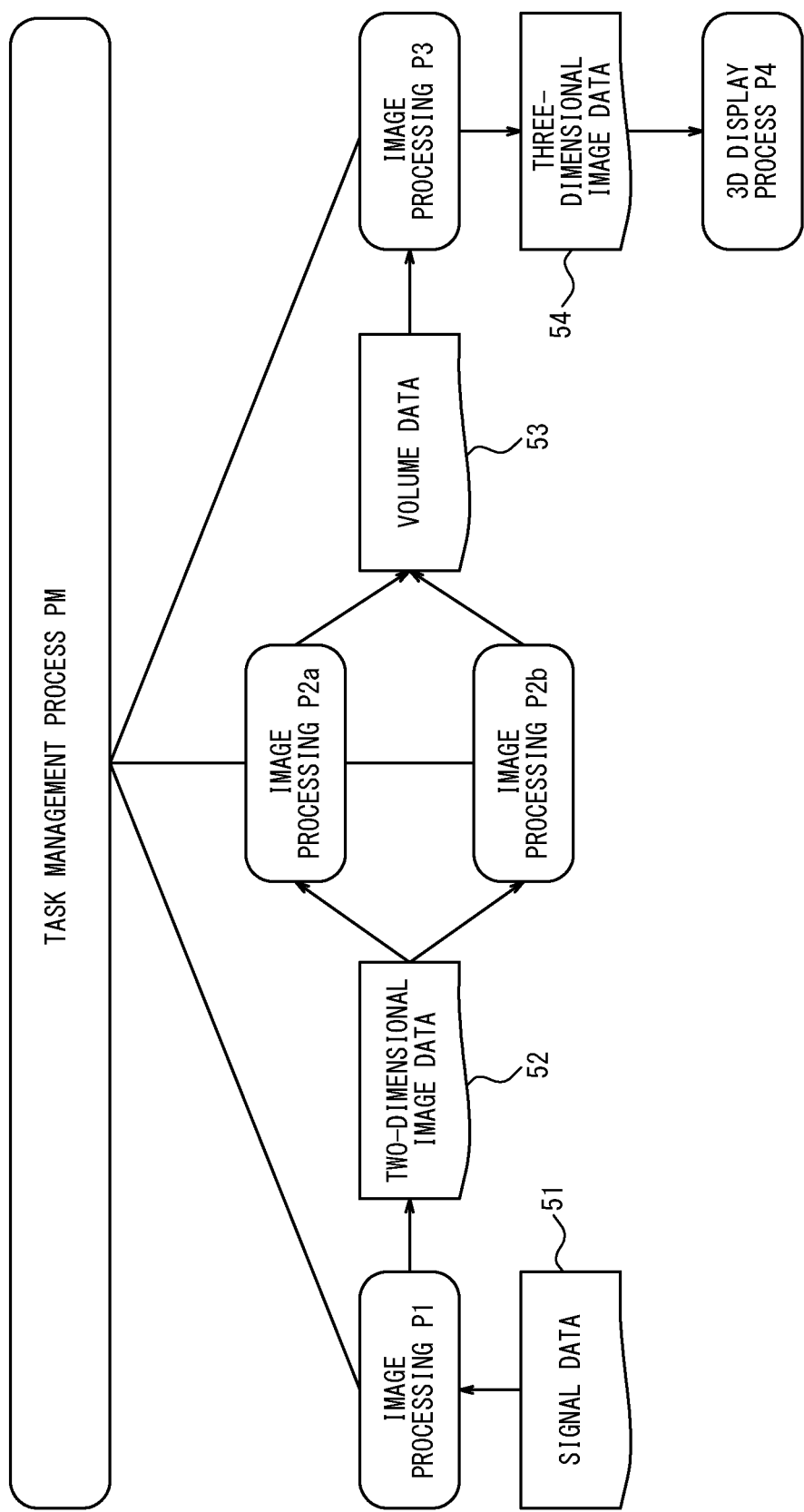
FIG. 14 is a diagram illustrating a data flow in a diagnosis support device according to a modification example of the embodiment of the present disclosure.

In a case of comparing with and without a preprocess, it is desirable to add a preprocessing layer in extracting the biological tissue region, but it is desirable not to add a preprocessing layer when determining a small object such as a catheter in a two-dimensional image. Therefore, as a modification example of the present embodiment, different image processing P2 may be prepared for each class. For example, as illustrated in FIG. 14, image processing P2a including a preprocessing layer for the biological tissue class and image processing P2b not including a preprocessing layer for the catheter class or for specifying a catheter position may be prepared.

In this modification example, the control unit 41 of the diagnosis support device 11 can smooth a two-dimensional image. In accordance with an exemplary embodiment, smoothing is a process of smoothing shading fluctuation for a pixel group. The smoothing includes the above-described smoothing. The control unit 41 executes a first classification process of classifying a plurality of pixels included in the two-dimensional image before being smoothed into the medical device class and one or more other classes. The control unit 41 executes a second classification process of classifying a pixel group excluding one or more pixels classified as the medical device class in the first classification process and included in the smoothed two-dimensional image into one or more classes including the biological tissue class. The control unit 41 can accurately display the medical device in a three-dimensional image by superimposing one or more pixels classified in the first classification process and the pixel group classified in the second classification process. As a further modification example of this modification example, the control unit 41 may execute a first classification process of classifying a plurality of pixels included in a two-dimensional image before being smoothed into the medical device class and one or more other classes, and a second classification process of smoothing the two-dimensional image excluding one or more pixels classified as the medical device class in the first classification process and classifying a pixel group included in the smoothed two-dimensional image into one or more classes including the biological tissue class.

In step S5, the control unit 41 of the diagnosis support device 11 measures a thickness of the biological tissue by using information regarding the biological tissue region acquired as a result of the classification in the image processing P2. The control unit 41 represents the thickness by reflecting the measurement result in the three-dimensional information. In step S6, the control unit 41 displays the thickness by adding a process such as separating colors of a stereoscopic structure by using gradation or the like. The control unit 41 may further provide additional information in a display method such as changing a color of a three-dimensional biological tissue structure for each class, such as a difference in the biological tissue property.

As described above, in the present embodiment, the control unit 41 analyzes the pixel group classified as the biological tissue class in step S4 and calculates a thickness of the biological tissue. The control unit 41 performs control of displaying the calculated thickness of the biological tissue. The display 16 is controlled by the control unit 41 to display the thickness of the biological tissue. As a modification example of the present embodiment, the control unit 41 may analyze the generated three-dimensional image of the biological tissue to calculate the thickness of the biological tissue.

The definition of the three-dimensional space in the present embodiment will be described.

As a three-dimensional processing method, a rendering method such as surface rendering or volume rendering, and various operations such as texture mapping, bump mapping, or environment mapping associated therewith are used.

The three-dimensional space used in the present embodiment is restricted to a size at which real-time processing can be performed. The size is required to conform to frames per second (FPS) at which an ultrasound image specified in the system is acquired.

In the present embodiment, the drive unit 13 capable of acquiring positions one by one can be used. The scanner unit 31 of the drive unit 13 can be moved on one axis, and the axis is set to a z axis and a position of the scanner unit 31 at a certain moment is set to z. The z axis is linked to one axis in a predefined three-dimensional space, and that axis is set to a Z axis. Since the Z axis and the z axis are linked, a point Z on the Z axis is predefined such that Z=f(z).

Information regarding the classification result 62 obtained through the image processing P2 is reflected on the Z axis. It is required that all the class information that can be classified in the image processing P2 can be stored in an XY-axis plane of the three-dimensional space defined here. In accordance with an exemplary embodiment, it can be desirable that the luminance information in the original ultrasound image is also included. As the information regarding the classification result 62 obtained through the image processing P2, all class information is reflected in the XY plane at a three-dimensional upper Z axis position corresponding to the current position of the scanner unit 31.

In addition, it can be desirable that the three-dimensional space is made three-dimensional by using volume rendering or the like for each Tx (=1/FPS), but the three-dimensional space cannot be increased infinitely because the processing time is limited. That is, the three-dimensional space is required to have a size that can be calculated within Tx (=1/FPS).

In a case where it is desired to convert a long range on the drive unit 13 into three dimensions, the long range may not fit in a size that can be calculated. Therefore, Z=f(z) is defined as appropriate conversion in order to restrict a range displayed by the drive unit 13 to the above range. This refers to that it can be necessary to set a function for converting a position on the Z axis into a position on the z axis within the limits of both a movement range of the scanner unit 31 of the drive unit 13 on the Z axis and a range in which the volume data 53 can be stored on the z axis.

As described above, in the present embodiment, the control unit 41 of the diagnosis support device 11 classifies a plurality of pixels included in a two-dimensional image generated by processing a signal of a reflected wave of ultrasound transmitted inside the biological tissue through which blood passes, into two or more classes including the biological tissue class corresponding to a pixel displaying the biological tissue. The control unit 41 generates a three-dimensional image of the biological tissue from a pixel group classified as the biological tissue class. The control unit 41 performs control of displaying the generated three-dimensional image of the biological tissue. Therefore, according to the present embodiment, the accuracy of the three-dimensional image generated from the two-dimensional image of ultrasound and representing a structure of the biological tissue can be improved.

According to the present embodiment, the three-dimensional image is displayed in real time, and thus an operator can perform a procedure without converting the two-dimensional image into the three-dimensional space in the head of the operator, so that it is expected that the operator's fatigue can be reduced and a procedure time can be shortened.

According to the present embodiment, a positional relationship of an insert such as a catheter or an implanted object such as a stent is clarified, and a failure in a procedure can be reduced.

According to the present embodiment, it is possible to understand the property of a biological tissue in three dimensions and thus to perform an accurate procedure.

According to the present embodiment, the accuracy can be improved by causing a preprocessing layer to be included in the image processing P2.

According to the present embodiment, a biological tissue thickness can be measured by using information regarding the classified biological tissue region, and the information can be reflected in three-dimensional information.

In the present embodiment, an ultrasound image is used as an input image, and output is classified by applying classification into two or more classes such as a region of a catheter body, a blood cell region, a calcification region, a fibrosis region, a catheter region, a stent region, a cardiac muscle necrosis region, an adipose biological tissue, or a biological tissue between the organs to each pixel or a region in which a plurality of pixels are regarded as a set, and thus it is possible to determine a corresponding portion from one image.

In the present embodiment, classification as at least a biological tissue class corresponding to the heart and blood vessel regions can be predefined. Learning efficiency can be improved by using, as a material for machine learning, supervised data classified by applying classification into two or more classes including this biological tissue class to each pixel or a region in which a plurality of pixels are regarded as a set.

In the present embodiment, the learned model 61 is constructed as any neural network for deep learning including a convolutional neural network (CNN), a recurrent neural network (RNN), and a long short-term memory (LSTM).

Figure 8:
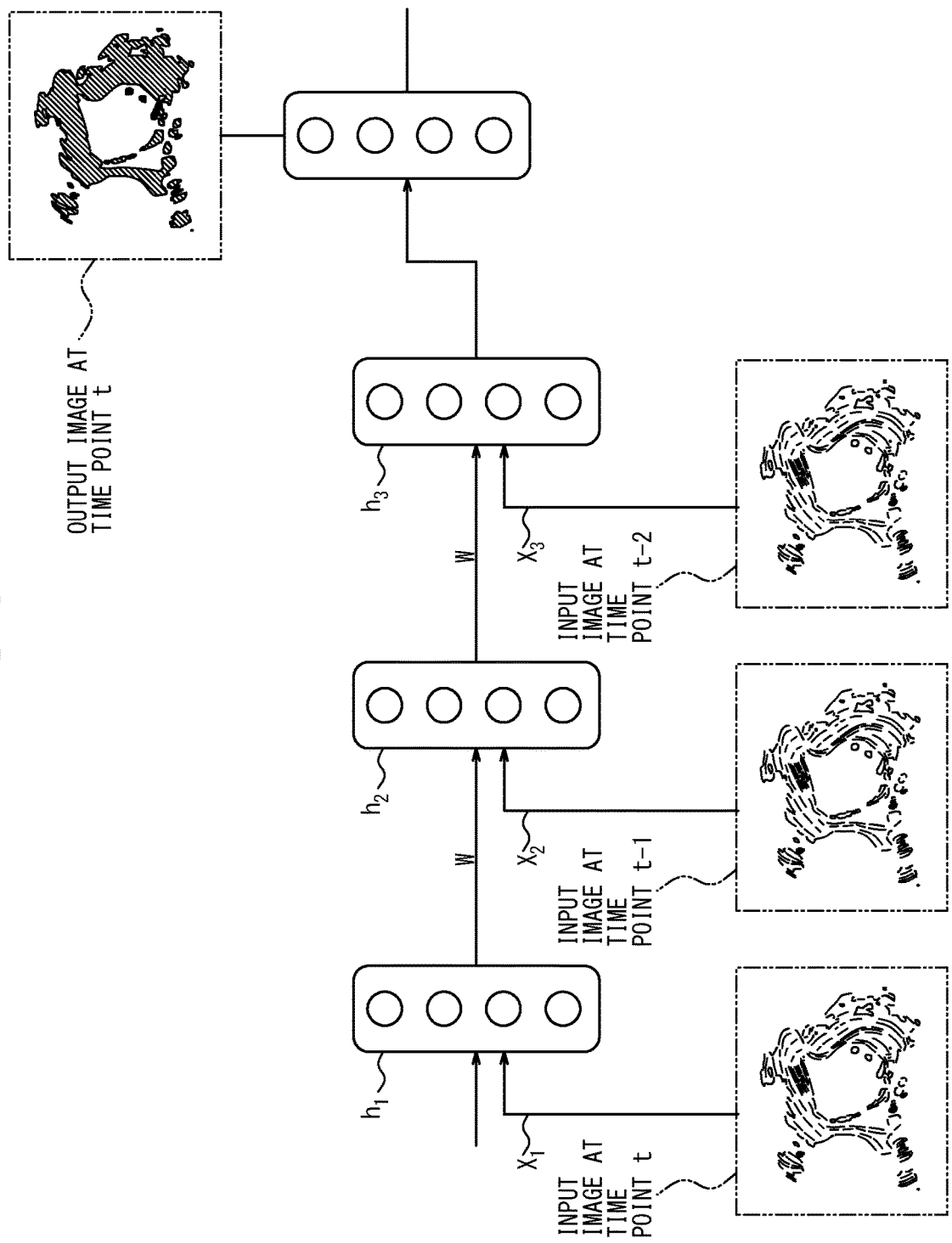
FIG. 8 is a diagram illustrating an example of implementing the learned model according to the embodiment of the present disclosure.

FIG. 8 illustrates an example of constructing the learned model 61 as an RNN.

In this example, time series are taken into consideration for classification. In a case where a position of a small object such as a catheter is determined, human beings generally take the continuity into consideration by changing an imaging location while changing a position of an ultrasound element. Similarly, in the image processing P2, a small object such as a catheter can be specified by taking into consideration the data on the time axis. In order to take the past information into consideration, the current classification is performed by inputting the past information for a certain period together with the currently obtained image into the image processing P2 at a time. The learned model 61 in this example is a model that receives at least a previously generated two-dimensional image and a generated new two-dimensional image as inputs, and outputs the classification result 62 of the generated new two-dimensional image. In FIG. 8, the input image at time point t−1 is the previously generated two-dimensional image, the input image at time point t is the generated new two-dimensional image, and the output image at time point t is the classification result 62 of the generated new two-dimensional image.

Figure 9:
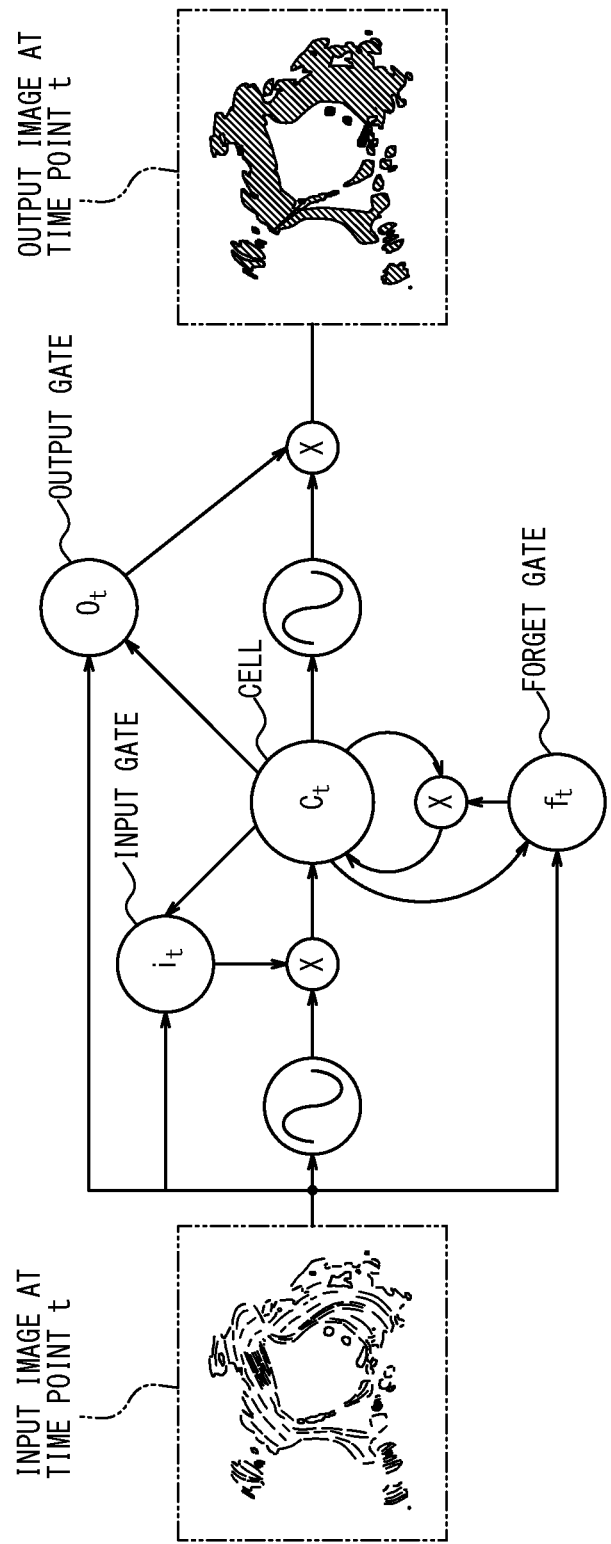
FIG. 9 is a diagram illustrating an example of implementing the learned model according to the embodiment of the present disclosure.

FIG. 9 illustrates an example of constructing the learned model 61 as an LSTM.

In this example, the learned model 61 has a memory module that stores two-dimensional images generated before two or more images. The memory module has a function of storing past information.

Figure 10:
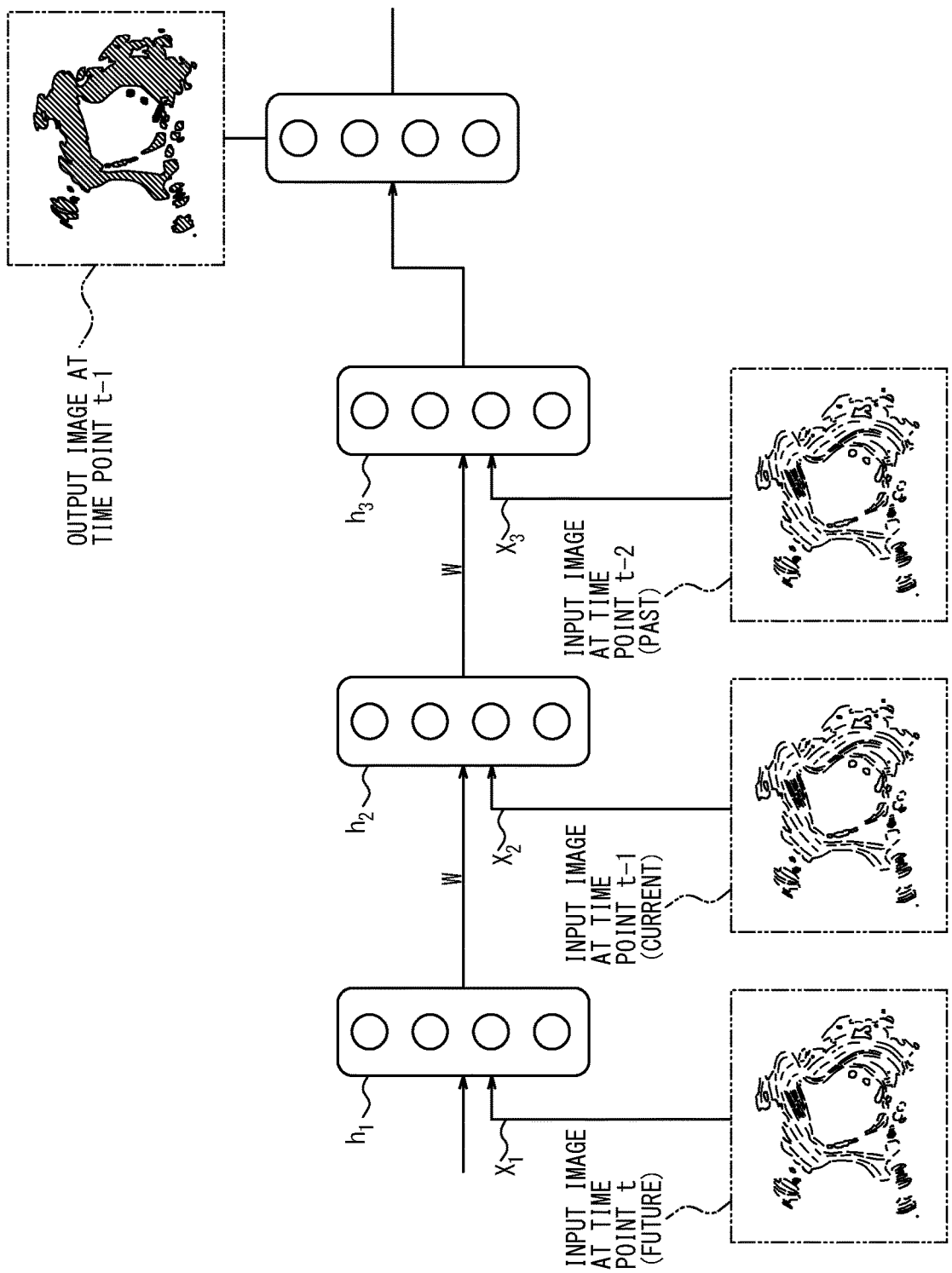
FIG. 10 is a diagram illustrating an example of implementing the learned model according to the embodiment of the present disclosure.

FIG. 10 illustrates an example of further taking future information into consideration.

In this example, the actual current time point is set as future time point t, an image for a certain period before time point t is input to the image processing P2, a time point slightly before the actual time point is set as current time point t−1, and an image at time point t−1 is classified. The learned model 61 in this example is a model that receives at least the previously generated two-dimensional image and a generated new two-dimensional image as inputs, and outputs the classification result 62 of the previously generated two-dimensional image. In FIG. 10, the input image at time point t−1 is the previously generated two-dimensional image, the input image at time point t is the generated new two-dimensional image, and the output image at time point t−1 is the classification result 62 of the previously generated two-dimensional image. The method in FIG. 10 may be applied to the example in FIG. 8 or 9.

As a method for extracting a small object such as a catheter in an image through deep learning, a method such as a region-based convolutional network (R-CNN), a Fast R-CNN, a Faster R-CNN, a Mask R-CNN, You Only Look Once (YOLO) or Single Shot MultiBox Detector (SSD) may be applied.

Figure 11:
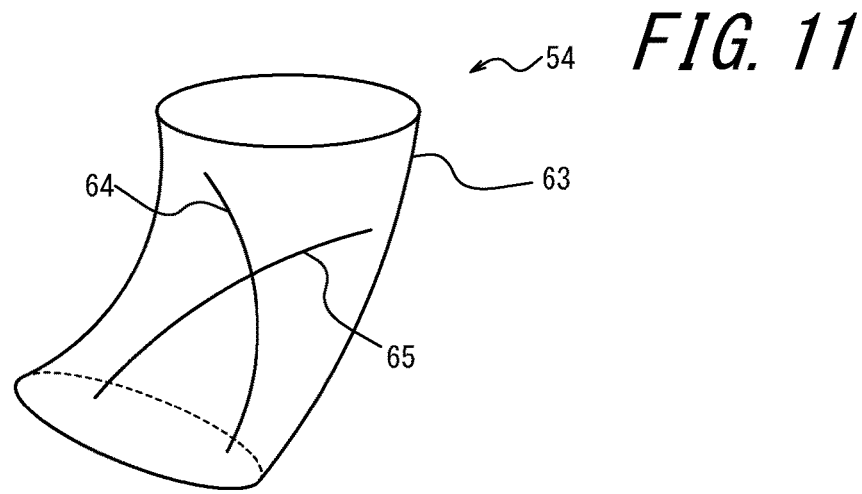
FIG. 11 is a diagram illustrating an example of a three-dimensional image according to the embodiment of the present disclosure.
Figure 12:
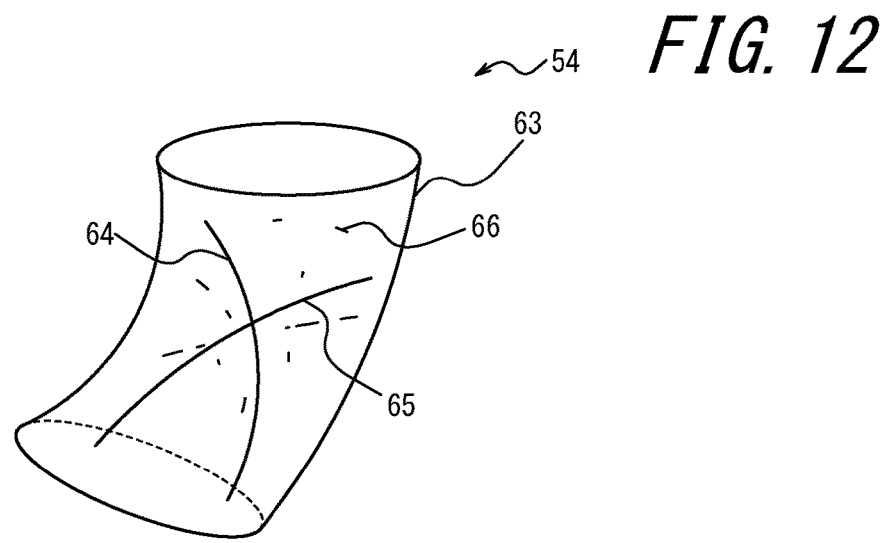
FIG. 12 is a diagram illustrating an example of a three-dimensional image according to the embodiment of the present disclosure.

As a modification example of the present embodiment, as illustrated in FIG. 11 or 12, the control unit 41 of the diagnosis support device 11 may determine whether one or more of a plurality of pixels included in a generated new two-dimensional image are to be classified as the medical device class on the basis of a classification result of a plurality of pixels included in the previously generated two-dimensional image. In this case, the control unit 41 compares the previously generated two-dimensional image with the generated new two-dimensional image. For example, in a case where one or more pixels having the coincidence of, for example, 90% or more with one or more pixels classified as the medical device class among the plurality of pixels included in the previously generated two-dimensional image are included in the generated new two-dimensional image, the control unit 41 classifies the one or more pixels included in the generated new two-dimensional image as the medical device class.

FIG. 11 illustrates an example of grouping.

In this example, in a case where a plurality of objects of a class in which a catheter or the like is expected to be continuously present are included in the three-dimensional space, the control unit 41 temporarily stores a result extracted by using the image processing P2. The control unit 41 classifies the extracted object group on the basis of information regarding the number of catheters given in advance by further taking into consideration time-series determination results. In FIG. 11, a blood vessel 63, a first catheter 64, and a second catheter 65 are independently reflected in the three-dimensional image data 54.

FIG. 12 illustrates an example of noise correction.

Even if positions of catheter and the like are extracted by using the image processing P2, all of the positions are not correct. Thus, in this example, the control unit 41 removes an obvious error by further taking into consideration the time-series determination results. In FIG. 12, the blood vessel 63, the first catheter 64, and the second catheter 65 are independently reflected in the three-dimensional image data 54. Although a noise 66 is illustrated in FIG. 12 for convenience, it is not actually reflected in the three-dimensional image data 54.

As a modification example of the present embodiment, a two-dimensional image based on IVUS may be generated a plurality of times by changing the presence or absence or disposition of a medical device inside a biological tissue. In that case, as illustrated in FIG. 13, the control unit 41 of the diagnosis support device 11 determines whether or not one or more of a plurality of pixels included in a generated new two-dimensional image are to be classified as the medical device class on the basis of a classification result of a plurality of pixels included in a previously generated two-dimensional image.

Figure 13:
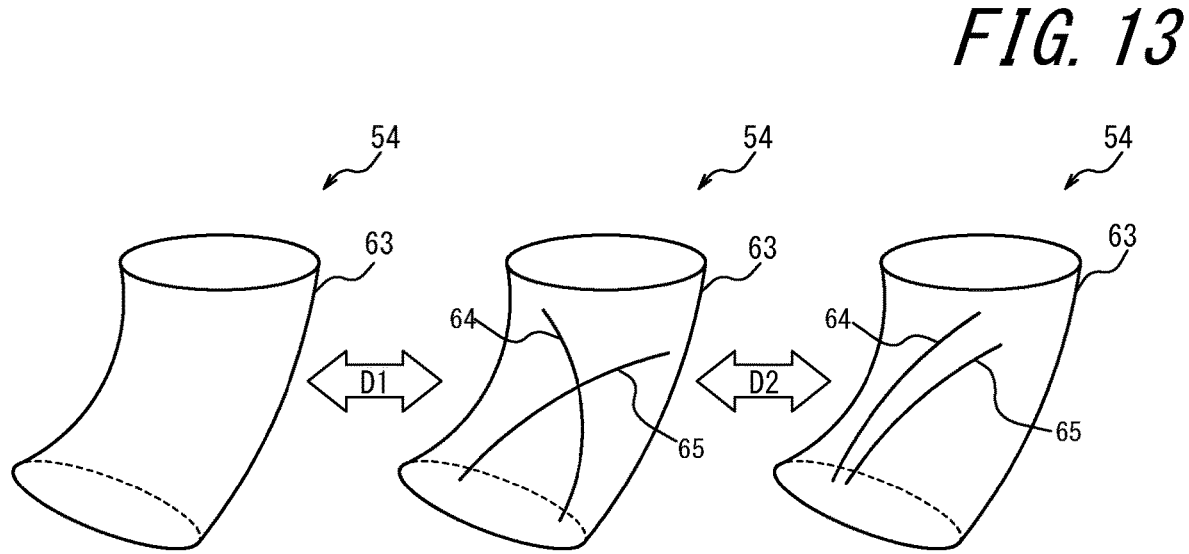
FIG. 13 is a diagram illustrating an example of a three-dimensional image according to the embodiment of the present disclosure.

In the example of FIG. 13, the first catheter 64 and the second catheter 65 can be reliably detected by comparing images captured with a difference D1 between the presence and absence of the catheter at the same position in the blood vessel 63. The first catheter 64 and the second catheter 65 can also be reliably detected by comparing images captured with a difference D2 between dispositions of the catheter at the same position in the blood vessel 63.

As a modification example of the present embodiment, instead of the diagnosis support device 11 performing the process in step S3, another device may perform the process in step S3, the diagnosis support device 11 may acquire the two-dimensional image generated as a result of the process in step S3 and perform the processes in and after step S4. That is, instead of the control unit 41 of the diagnosis support device 11 processing an IVUS signal to generate a two-dimensional image, another device may process the IVUS signal to generate the two-dimensional image and input the generated two-dimensional image to the control unit 41.

The present disclosure is not limited to the above embodiment. For example, a plurality of blocks shown in the block diagram may be integrated, or one block may be divided. Instead of executing the plurality of steps shown in the flowchart in a time series according to the description, the steps may be executed in parallel or in a different order according to the processing capacity of a device that executes each step, or as necessary. Other changes are possible without departing from the spirit of the present disclosure.

For example, the image processing P1, the image processing P2, and the image processing P3 illustrated in FIG. 6 may be executed in parallel.

The detailed description above describes embodiments of a diagnosis support device, a diagnosis support system, and a diagnosis support method. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A diagnosis support device comprising:
a control unit configured to:
correlate a plurality of pixels included in a two-dimensional image with two or more classes including a biological tissue class, the two-dimensional image being generated by using a signal of a reflected wave of ultrasound transmitted inside a biological tissue through which blood passes and the two-dimensional image including the biological tissue;
generate a three-dimensional image of the biological tissue from a pixel group correlated with the biological tissue class; and
perform control of displaying the generated three-dimensional image of the biological tissue,
wherein the control unit is configured to process the signal of the reflected wave to generate the two-dimensional image at a speed of 15 frames per second to 90 frames per second, and, by processing one two-dimensional image within 11 msec to 66 msec on a graphics processing unit, generate the three-dimensional image of the biological tissue corresponding to a new two-dimensional image at a speed of 15 frames per second to 90 frames per second before generating a subsequent two-dimensional image each time the new two-dimensional image is generated so as to update the three-dimensional image in real time.

2. The diagnosis support device according to claim 1,
wherein the two or more classes further include a blood cell class, and
the control unit is configured to exclude a pixel group correlated with the blood cell class from the plurality of pixels to generate the three-dimensional image of the biological tissue.

3. The diagnosis support device according to claim 1, wherein the control unit is configured to analyze either the pixel group correlated with the biological tissue class or the generated three-dimensional image of the biological tissue to calculate a thickness of the biological tissue, and to perform control of displaying the calculated thickness of the biological tissue.

4. The diagnosis support device according to claim 1,
wherein the two or more classes further include a medical device class, and
the control unit is configured to generate a three-dimensional image of the medical device from one or more pixels correlated with the medical device class, and to performs control of displaying the generated three-dimensional image of the biological tissue and the three-dimensional image of the medical device in a form distinguishable from each other.

5. The diagnosis support device according to claim 4,
wherein the control unit is configured to execute a first classification process of correlating the plurality of pixels included in the two-dimensional image with the medical device class and one or more other classes, and a second classification process of smoothing the two-dimensional image excluding one or more pixels correlated with the medical device class in the first classification process and of correlating a pixel group included in the smoothed two-dimensional image with one or more classes including the biological tissue class.

6. The diagnosis support device according to claim 4,
wherein the control unit is configured to execute a first classification process of smoothing the two-dimensional image and of correlating the plurality of pixels included in the two-dimensional image before being smoothed with the medical device class and one or more other classes, and a second classification process of correlating, with one or more classes including the biological tissue class, a pixel group included in the smoothed two-dimensional image excluding one or more pixels correlated with the medical device class in the first classification process.

7. The diagnosis support device according to claim 4, wherein, in a case where one or more pixels correlated with the medical device class include two or more pixels displaying different medical devices, the control unit is configured to generate the three-dimensional images of the medical devices for each medical device, and to perform control of displaying the generated three-dimensional images of the medical devices in a distinguishable form for each medical device.

8. The diagnosis support device according to claim 4, wherein the two-dimensional image is sequentially generated while changing a transmission position of the ultrasound inside the biological tissue, and the control unit is configured to determine whether or not to correlate one or more pixels among the plurality of pixels included in the generated new two-dimensional image with the medical device class on the basis of a correlation result of the plurality of pixels included in the two-dimensional image generated before.

9. The diagnosis support device according to claim 1, wherein the control unit is configured to correlate the plurality of pixels included in the two-dimensional image by using a learned model.

10. The diagnosis support device according to claim 1, wherein the control unit includes a processor and the graphic processing unit, the processor configured to process the signal of the reflected wave to generate the two-dimensional image at the speed of 15 frames per second to 90 frames per second, and the graphics processing unit configured to process the one two-dimensional image within 11 msec to 66 msec to generate the three-dimensional image of the biological tissue.

11. A diagnosis support system comprising:
the diagnosis support device according to claim 1; and
a probe that is configured to transmit the ultrasound inside the biological tissue and input the signal of the reflected wave to the control unit.

12. A diagnosis support method comprising:
transmitting, by a probe, ultrasound inside a biological tissue through which blood passes;
correlating, by a diagnosis support device, a plurality of pixels included in a two-dimensional image that is generated by using a signal of a reflected wave of the ultrasound and includes the biological tissue with two or more classes including a biological tissue class;
generating, by the diagnosis support device, a three-dimensional image of the biological tissue from a pixel group correlated with the biological tissue class; and
displaying, by a display, the three-dimensional image of the biological tissue generated by the diagnosis support device,
wherein the diagnosis support method further comprises processing the signal of the reflected wave to generate the two-dimensional image at a speed of 15 frames per second to 90 frames per second, and
the generating, by processing one two-dimensional image within 11 msec to 66 msec on a graphics processing unit, generates the three-dimensional image of the biological tissue corresponding to a new two-dimensional image at a speed of 15 frames per second to 90 frames per second before generating a subsequent two-dimensional image each time the new two-dimensional image is generated so as to update the three-dimensional image in real time.

13. The diagnosis support method according to claim 12, wherein the two or more classes further include a blood cell class, further comprising:
excluding a pixel group correlated with the blood cell class from the plurality of pixels to generate the three-dimensional image of the biological tissue.

14. The diagnosis support method according to claim 12, further comprising:
analyzing either the pixel group correlated with the biological tissue class or the generated three-dimensional image of the biological tissue to calculate a thickness of the biological tissue; and
displaying the calculated thickness of the biological tissue.

15. The diagnosis support method according to claim 12, wherein the two or more classes further include a medical device class, further comprising:
generating a three-dimensional image of the medical device from one or more pixels correlated with the medical device class; and
displaying the generated three-dimensional image of the biological tissue and the three-dimensional image of the medical device in a form distinguishable from each other.

16. The diagnosis support method according to claim 12, further comprising:
performing the processing of the signal of the reflected wave to generate the two-dimensional image at the speed of 15 frames per second to 90 frames per second on a central processing unit.

17. A non-transitory computer readable medium (CRM) storing computer program code executed by a computer processor that executes a process for diagnosis support, the process comprising:
correlating a plurality of pixels included in a two-dimensional image with two or more classes including a biological tissue class, the two-dimensional image being generated by using a signal of a reflected wave of ultrasound transmitted inside a biological tissue through which blood passes and the two-dimensional image including the biological tissue;
generating a three-dimensional image of the biological tissue from a pixel group correlated with the biological tissue class; and
displaying the generated three-dimensional image of the biological tissue,
wherein the process further comprises processing the signal of the reflected wave to generate the two-dimensional image at a speed of 15 frames per second to 90 frames per second, and
the generating, by processing one two-dimensional image within 11 msec to 66 msec on a graphics processing unit, generates the three-dimensional image of the biological tissue corresponding to a new two-dimensional image at a speed of 15 frames per second to 90 frames per second before generating a subsequent two-dimensional image each time the new two-dimensional image is generated so as to update the three-dimensional image in real time.

18. The non-transitory computer readable medium according to claim 17, wherein the two or more classes further include a blood cell class, further comprising:
excluding a pixel group correlated with the blood cell class from the plurality of pixels to generate the three-dimensional image of the biological tissue.

19. The non-transitory computer readable medium according to claim 17, further comprising:
analyzing either the pixel group correlated with the biological tissue class or the generated three-dimensional image of the biological tissue to calculate a thickness of the biological tissue; and
displaying the calculated thickness of the biological tissue.

20. The non-transitory computer readable medium according to claim 17, wherein the two or more classes further include a medical device class, further comprising:
generating a three-dimensional image of the medical device from one or more pixels correlated with the medical device class; and
displaying the generated three-dimensional image of the biological tissue and the three-dimensional image of the medical device in a form distinguishable from each other.

* * * * *